United States Patent [19]
Hays et al.

[11] Patent Number: 5,092,346
[45] Date of Patent: Mar. 3, 1992

[54] DENTAL ORTHOSIS FOR ALLEVIATION OF SNORING

[75] Inventors: Marvin B. Hays; Thomas E. Meade, both of Albuquerque, N. Mex.

[73] Assignee: Hays & Meade, Inc., Albuquerque, N. Mex.

[21] Appl. No.: 616,745

[22] Filed: Nov. 16, 1990

Related U.S. Application Data

[63] Continuation-in-part of Ser. No. 253,388, Oct. 3, 1988, abandoned, which is a continuation-in-part of Ser. No. 107,670, Oct. 13, 1987, abandoned.

[51] Int. Cl.$^5$ ............................................. A61F 5/56
[52] U.S. Cl. ................................... 128/848; 128/859; 128/861
[58] Field of Search ........................ 128/846–848, 128/859–863

[56] References Cited

U.S. PATENT DOCUMENTS

| | | | |
|---|---|---|---|
| 746,869 | 12/1903 | Moulton | 128/136 |
| 1,674,336 | 6/1928 | King | 128/136 |
| 2,424,533 | 7/1947 | Faires | 128/136 |
| 2,521,039 | 9/1950 | Carpenter | 128/136 |
| 2,590,118 | 3/1952 | Oddo, Jr. | 128/861 |
| 2,882,893 | 4/1959 | Godfroy | 128/136 |
| 3,434,970 | 3/1969 | Strickland | 128/136 |
| 3,457,916 | 7/1969 | Wolicki | 128/136 |
| 3,871,370 | 3/1975 | McDonald | 128/860 |
| 4,114,614 | 9/1978 | Kesling | 128/136 |
| 4,304,227 | 12/1981 | Samelson | 128/136 |
| 4,495,945 | 1/1985 | Liegner | 128/136 |
| 4,568,280 | 2/1986 | Ahlin | 433/6 |
| 4,593,686 | 6/1986 | Llcyd | 128/136 |

FOREIGN PATENT DOCUMENTS

| | | | |
|---|---|---|---|
| 2320501 | 11/1974 | Fed. Rep. of Germany | 335/728 |
| 1569129 | 6/1980 | United Kingdom . | |

*Primary Examiner*—Robert A. Hafer
*Assistant Examiner*—Kevin G. Rooney
*Attorney, Agent, or Firm*—Cushman, Darby & Cushman

[57] ABSTRACT

A dental orthosis is provided for use in the treatment of snoring. The upper portion of the device receives the upper teeth of a user. Once properly fitted, the device will firmly grip all upper teeth forward of the premolars and remain positioned independent of natural motions of the lower jaw. The lower portion of the device is formed into a ramp structure whereby natural jaw motions result in the engagement of the lower teeth against the ramp, which will cam the lower jaw into a more forward position. An aperture in the device between the upper portion and the lower portion facilitates the passage of air for mouth breathing and attracts the tongue forward. By inducing the lower jaw and tongue to a more forward position, the device induces a more open posterior airway in the user, resulting in a significant reduction in snoring.

18 Claims, 3 Drawing Sheets

DENTAL ORTHOSIS FOR ALLEVIATION OF SNORING

This is a continuation-in-part application filed under the authority of 37 C.F.R. 1.62 to add and claim additional disclosure not revealed in an application by the same inventors and identified as Ser. No. 07/253,388, filed on Oct. 3, 1988, for Silencer, now abandoned, which was a continuation-in-part of an application by the same inventors and identified as Ser. No. 07/107,670, filed Oct. 13, 1987 and now abandoned.

BACKGROUND OF THE INVENTION

1. Field of Invention

Snoring is normally the result of vibration of the uvula, soft palate, and adjacent structures during sleep and signals partial obstruction due to the narrowing of the upper airway at that site. In most cases of snoring, breathing is normal or minimally impaired, and symptoms primarily concern sleep disturbance and the social consequences of snoring. In others, snoring is associated with the obstructive sleep apnea syndrome, a serious condition characterized by intermittent upper airway obstructions that require arousal for relief.

This invention relates to a dental orthosis for use in reducing snoring. It is adapted to be placed within the mouth and in the dental arch defined by the upper teeth. The device may be fitted to the wearer by a professional in the dental arts or by the layman.

The upper portion of the device consists of a trench to receive the upper teeth. Once properly fitted, the device will firmly grip all upper teeth forward of the premolars and remain positioned independent of natural motions of the lower jaw. The lower portion of the device is formed into a ramp structure whereby natural jaw motions, including the bite reflex, encourage the engagement of the user's lower teeth against the ramp, which will cam the lower jaw into a more forward position. An aperture in the device between the upper portion and the lower portion facilitates the passage of air for mouth breathing and attracts the tongue forward. By inducing the lower jaw and tongue to a more forward position, the device induces a more open airway in the user resulting in a significant reduction in snoring.

2. Description of the Prior Art

Various devices are known in the art intended for the reduction of snoring, as are other oral devices to be received in the mouth to prevent or reduce damage to the oral cavity during athletic competition, such as boxing or football.

The athletic mouth guards are intended to prevent the abrading of the soft tissue of the lips and cheeks against the teeth and to prevent the upper and lower teeth from forcibly engaging one another, with resultant and permanent mechanical damage.

Various snore reducing devices intended for placement in the oral cavity are known in the prior art. Some are arranged to seal the lips of the wearer, one to another, thus blocking the mouth. Others recognize that portions of the uvula, soft palate, and adjacent structures vibrate during sleep in response to the passage of air past these tissues, and thereby attempt to minimize such vibrations by sharply reducing the volume of air passing through the mouth without necessarily completely blocking the mouth. However, if the nose is blocked, or partially blocked, this reduction of the airway increases the velocity of the air passing those tissues and snoring can actually increase.

An example of prior art devices is found in U.S. Pat. No. 1,674,336 issued to King for Respirator. King intends that his device will maintain a plentiful supply of oxygen to the blood of a user during sleep, and even reduce snoring. His structure comprises an upper channel and a lower channel to receive and hold apart the upper and the lower teeth, respectively. The two channels are spaced apart vertically to prop the upper and lower front teeth apart. The invention includes a central air passage which opens into the upper and lower channels. Projections from the sides of the upper channel support the tongue in an elevated position and define between them an air channel.

The King device much resembles an athletic mouthguard. It includes an upper channel and a lower channel to receive the teeth of the user and provides for an air passage between the channels. In use, the device props the teeth of a user apart in a fixed position so that air may pass in and out of the mouth more freely during sleep through the central air passage. Projections from the upper channel support the tongue in an elevated position to prevent blocking of the air passage. The device moves the lower jaw downward, which King claims opens the posterior airway to facilitate the passage of air to and from the throat and lungs. As the device receives the top and bottom teeth and fixes their relative position, natural mouth motions, including motion of the lower jaw, are prevented.

In contradistinction to the teachings discussed above, the invention described hereinafter does not fix the position of the upper and lower jaws and tongue. Instead, by an adroit arrangement of structure, the device attaches firmly to the upper jaw, while allowing natural mouth movements and motions of the lower jaw and teeth, and tongue. The present invention further is distinguished in providing a ramp to engage the lower anterior teeth and induce forward movement of the lower jaw, resulting in the opening of the posterior airway. King makes no provision for a ramp. It provides for only a lower trench with sides to accommodate the lower jaw and fix it's position.

SUMMARY OF THE INVENTION

It is a broad object of the invention to provide a dental orthosis to be inserted into the oral cavity of a user to eliminate or substantially reduce snoring during sleep.

It is a further object of the invention to provide a dental orthosis to be removably fitted to the crowns of some of the upper teeth of a user to maintain a spacing between the upper and lower teeth.

It is a yet further object of the invention to provide a dental orthosis having a trench to receive some of the user's upper teeth and a ramp formed on the bottom portion to cam the lower jaw forward without entraining the lower jaw, and thus to provide a more open posterior airway.

It is a yet further object of the invention to provide a dental orthosis which is comfortable in use and which while in use facilitates natural movement of the lower jaw and attached tissues and natural functions such as swallowing and yawning.

Other objects of the invention will become apparent as the specification progresses, reference being had to the accompanying drawings.

DETAILED DESCRIPTION OF A PREFERRED EMBODIMENT

As illustrated in FIGS. 1-5B, inclusive, the dental orthosis for reducing snoring of the present invention comprises a structure shaped to conform to the upper dental arch of a user and extending at least between the pre-molar teeth on each side of the wearer's mouth.

The device may be formed from a single piece of methylmethacrylate, which is a plastic material used for dentures. After the fitting of the device, it is cured to prevent absorption of mouth fluids, or cleaning fluids, and to present a smooth non-irritating surface to the soft tissues of the mouth.

However, the device may preferably be composed of a resilient semi-rigid polycarbonate resin thermoplastic having good physical characteristics and having a specific gravity of about 1.20, a tensile strength (yield) of about 9000 and a softening temperature of about 310 degrees F. An example of such resin is sold by the General Electric Company under the Registered Trademark LEXAN. The material provides a framework for the device, and it is used in conjunction with an additional resin material further discussed below.

In the preferred embodiment, a substantial advantage to the user and to the fitter is offered when another resin layer is bonded to the polycarbonate resin thermoplastic device described above, such layer composed of an ethylene-vinyl acetate copolymer resin having a softening and molding temperature of about 150 degrees F. An example of such resin is sold by the Du Pont Company under the Registered Trademark ELVAX.

As will later be more fully explained, this preferred embodiment can be easily molded in the user's mouth to conform to the configuration of the user's upper teeth, thus saving time to fabricate, fit, and adjust the device and resulting in significant cost savings over a similar device requiring the use of molds and the services of a dental laboratory in its construction.

In either species of the invention, the lower anterior teeth of the user engage the device only at a ramp surface whereby natural lower jaw and teeth motions are preserved. The lower anterior teeth naturally strike the ramp and are induced by natural jaw movements to advance along the ramp moving the lower jaw into a more forward position, for a purpose that will later be more fully explained.

Figure 6:
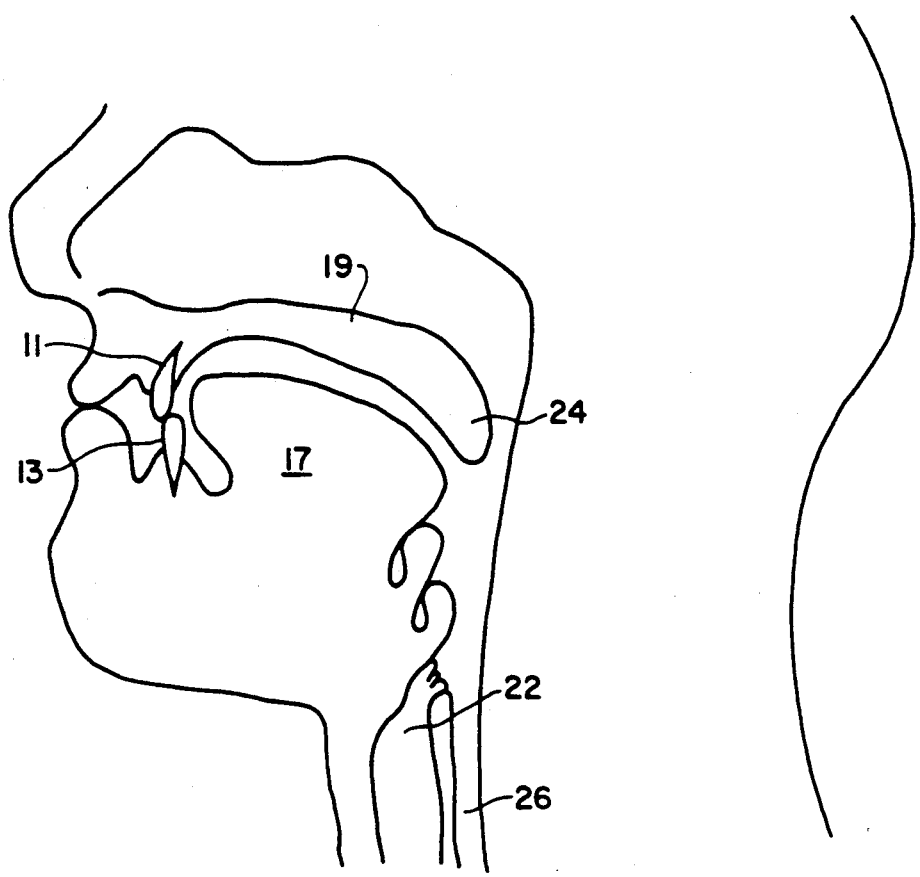
FIG. 6 is a partial elevation in cross section of a human head and neck.
Figure 7:
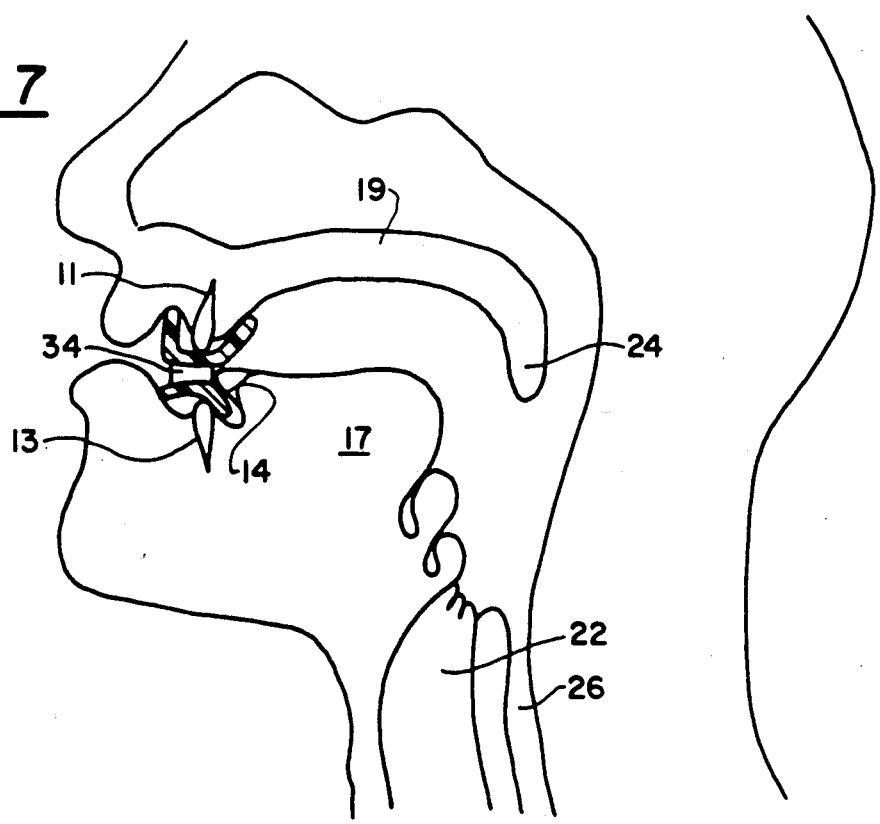
FIG. 7 is a partial elevation in cross section of the human head and neck of FIG. 6 showing the dental orthosis in place.

FIGS. 6 and 7, respectively, show the normal position of the human jaw and air passages and the position of the jaw and the increased volume of the air passages when the preferred embodiment of the present invention is in use. As compared to FIG. 6, FIG. 7 shows the lower jaw in an advanced position and an increase in the volume of the airway.

Figure 1:
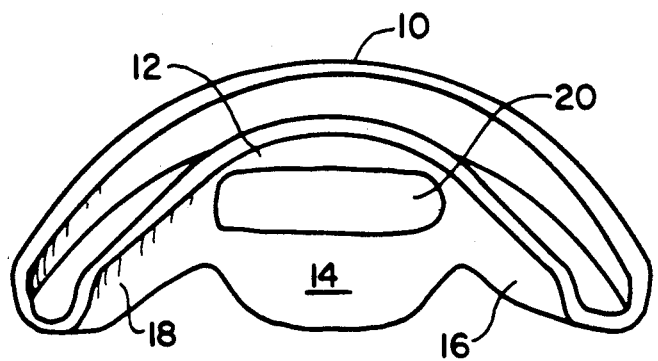
FIG. 1 is a perspective view of one species of the dental orthosis of the invention.
Figure 2:
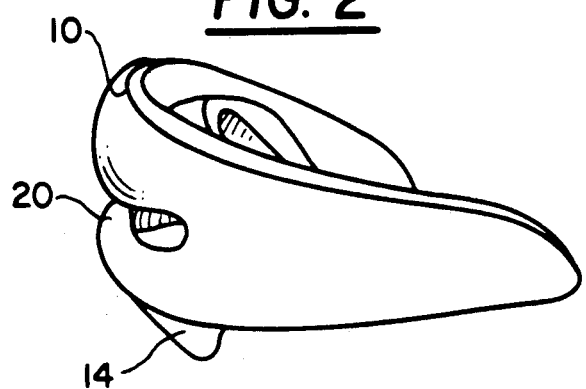
FIG. 2 is a side elevation of the device of FIG. 1.
Figure 3:
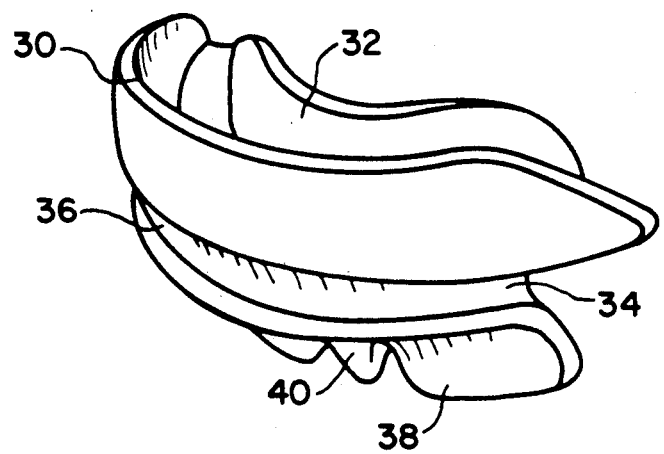
FIG. 3 is a perspective view of another species of the invention.
Figure 4:
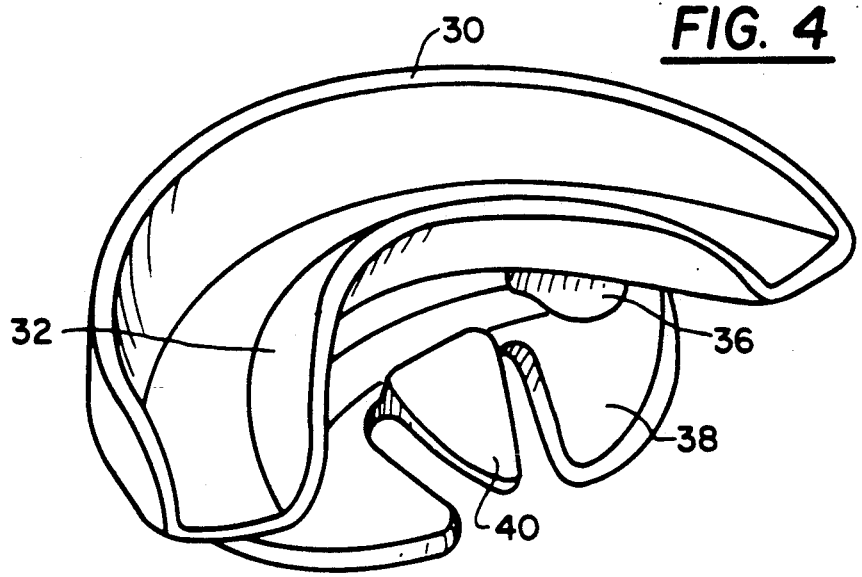
FIG. 4 is a rearward view of the device of FIG. 3.

Considering now FIGS. 1 and 2, the dental orthosis comprises a semicircular structure substantially triangular in side elevation and having an outer boundary area defining an upper rim, reference character 10, corresponding to the user's dental arch and a rearward wall, 12, forming a teeth receiving trench between rim 10 and wall 12. A curved ramp 14 starting at the lower outer boundary area of the device extends rearwardly at an angle of about 60 degrees from the horizontal to bridge laterally between the lower extremities of wall 12. An aperture 20 pierces the forward surface of the device. The bottom of the trench is substantially horizontal when the device is in use.

Figure 5A:
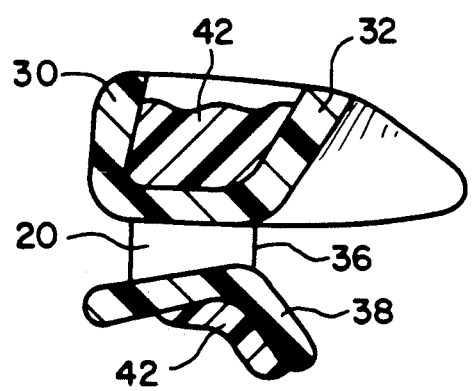
FIG. 5A is a side elevation in section of the species of FIG. 3.
Figure 5B:
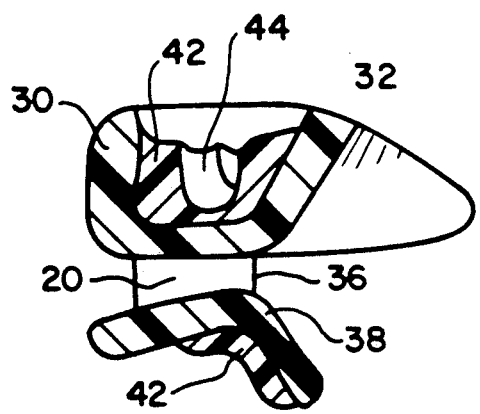
FIG. 5B is a second side elevation in section of the species of FIG. 3.

Attention is now invited to the species of the invention revealed in FIGS. 3, 4, 5A, 5B. In order to form a more generous air passage in the semi-circular structure, an upper rim 30 and a wall 32 form a teeth-receiving trench. A pair of stanchions 34 and 36 join the ramp structure 38 to the upper body. The ramp 38 has formed therein a triangular leaf 40 which has been found desirable for ease of application and durability of the applied acetate copolymer resin layer. In another configuration (not shown), the ramp structure 38 has a uniform upper and lower surface, and an aperture, or a series of apertures, are provided to facilitate the application of the resin layer and to increase its durability on the structure. This resin layer previously described is shown by reference to FIGS. 5A and 5B. FIG. 5A shows the species of the device revealed in FIGS. 3 and 4 in cross section. A layer of acetate copolymer resin 42 is shown applied to the teeth-receiving trench and to the ramp 38. FIG. 5B is the same cross-sectional view as found in FIG. 5A. The only difference is that FIG. 5B shows a tooth depression 44 in the acetate copolymer resin layer resulting from the fitting of the device to a user.

Referring again to FIGS. 6 and 7, FIG. 6 shows the normal position of the teeth and jaw and that upper teeth 11 overlie and are in front of lower teeth 13. The tip of tongue 17 is proximate to the teeth as shown. Palate 19 terminates in the uvula 24 and a normal spacing is shown between these members and the tongue 17. Air passages lead to the trachea 22, which lies next to the esophagus 26.

When either species of this invention is in situ, as revealed in the cross section view of FIG. 7, upper teeth 11 are received in the trench formed between rim 10 and wall 12 (FIGS. 1 and 2). Normal mouth motions, such as clenching of the jaw as a result of the bite reflex during sleep, will cause the lower teeth to engage against ramp 14. The result of such engagement is to cam and urge the lower jaw forward along the ramp, whereby the lower teeth 13 lie more nearly even with the upper teeth 11 and there is a spacing between the teeth. The result of this interaction on airway structures is disclosed in FIG. 7 where, as compared against FIG. 6, an increased spacing is seen between the tongue and palate and uvula. The larger volume now available reduces the velocity of air during breathing, and palate and uvula vibrations are reduced or eliminated because the soft tissues previously entrained by air passage no longer vibrate or oscillate, or do so at a reduced frequency.

It is important to note that relatively minor forward movement of the lower jaw, in the range of 2 to 6 mm, serves to reduce the incidence of snoring. As is the case with any orthosis, further adjustment of the device to the user may be desirable from time to time.

Aperture 20 serves a dual function in the structure. If the nose is blocked or partially blocked, it allows ease of the passage of air for mouth breathing. If the nose is unblocked, the tongue, which by the nature of its nerve responses seeks a cavity, as anyone who has a cavity in a tooth will bear witness, and will seek the aperture 20 formed between flaring walls 16 and 18 (FIG. 1) and will engage the aperture thus moving the tongue forward and further increasing its distance from the palate and uvula. This movement of the tongue forward further opens the air passage behind the tongue.

When the device is formed from the polycarbonate resin-thermoplastic having the layer of acetate copolymer resin bonded thereto at the teeth-engaging surfaces, namely the trench which receives the upper teeth and the ramp which receives the lower teeth, then individual fitting of the device to the user is greatly simplified. The acetate copolymer resin layer is about 3 to 4 millimeters in thickness in the trench and a coating of the material approximately 2 to 3 millimeters thick is applied to the ramp. The acetate copolymer resin has a substantially lower softening and molding temperature than that of the polycarbonate resin-thermoplastic forming the device, per se, and thus individual fitting to the user's mouth is simplified. An immersion of the device in a hot fluid, preferably water, prior to the fitting serves to impart a yielding nature to the acetate copolymer resin layer whereby it accepts the user's distinctive tooth configuration during the fitting process. Once the acetate copolymer resin is sufficiently moldable, the device is forcibly inserted against the user's upper jaw and teeth. Upon cooling to ambient temperature, the acetate copolymer resin retains the user's tooth configuration, for ease of repeat placement by the user. Excess resin can be cut from the device to make the device more comfortable in use. Additional minor adjustment is often advisable to increase comfort for the user or to modify the alignment of the device. If extensive dental work is later performed or if mechanical damage occurs, a new fitting may be necessary for mechanical comfort and ease of use.

The preferred embodiment reduces the time and cost of fitting the device to a minimum. There is no need for the use of molds or employing the services of dental laboratories. The device can be fitted to the user by a dentist in a matter of minutes. With proper instructions and safeguards, the device could also be self-fitted by a user or fitted to a user by a friend or family member.

The scope of this invention is not intended to be limited by the particular embodiments and specific constructions described herein, but should be defined only by the appended claims and reasonable equivalents thereof.

We claim:

1. A dental orthosis for removable placement in the mouth of a patient to maintain a predetermined gap between and relative orientation of the upper and lower teeth of that patient to thereby reduce snoring experienced by that patient, comprising:
    an upper element having a curved shape which substantially corresponds to the shape of an upper dental arch, said upper element having an upwardly open tooth receiving trench for receiving at least a portion of at least some of the upper teeth of the patient; and
    a ramp element operatively coupled to and extending downwardly from said upper element, said ramp element having a ramp surface for engaging at least some of the lower anterior teeth of the patient, said upper element and said ramp element being operatively interconnected and configured for a particular patient so that when the upper teeth of that patient are received in the tooth receiving trench of said upper element, the ramp element extends forwardly with respect to a vertical plane of the lower anterior teeth of that patient when that patient's lower jaw is in an unstressed position so that engagement of said ramp surface with the lower teeth of that patient positively shifts that patient's lower jaw forwardly with respect to said unstressed position whereby snoring experienced by that patient is reduced.

2. A dental orthosis as in claim 1, further comprising means defining an aperture for allowing the passage of air into and from the mouth.

3. A dental orthosis as in claim 1, wherein said ramp element is spaced from said upper element so as to define an elongated aperture therebetween for the passage of air.

4. A method of reducing snoring during sleep, comprising the steps of:
    guiding into a patient's oral cavity a pre-formed device selected for that patient which includes:
    an upper element having a curved shape which substantially corresponds to the shape of an upper dental arch, said upper element having an upwardly open tooth receiving trench for receiving at least a portion of at least some of the upper teeth of the patient; and
    a ramp element operatively coupled to and extending downwardly from said upper element, said ramp element having a ramp surface for engaging at least some of the lower anterior teeth of the patient, said ramp element being operatively coupled to said upper element so that when the upper teeth of the patient are received in the tooth receiving trench of the upper element, the ramp element extends forwardly with respect to a vertical plane of the lower anterior teeth when the lower jaw is in an unstressed position so that engagement of said ramp surface and said lower teeth positively shifts the lower jaw forwardly with respect to said unstressed position;
    introducing the patient's upper teeth into said tooth receiving trench; and
    slidingly engaging the patient's lower teeth with the ramp surface of the ramp element, thereby predeterminately spacing the upper and lower teeth and shifting the lower jaw forwardly with respect to said unstressed position so as to increase an air passage through the oral cavity.

5. A method as in claim 4, wherein the lower jaw bite reflex and teeth motions against the ramp element move the lower jaw forward to increase spacing between the tongue and palate and uvula.

6. A method as in claim 4, wherein the device is configured and fitted so that the tongue of the wearer will reposition itself in an anterior position by seeking an aperture formed in the forward area of the device, thereby increasing it's upper spacing from the palate and the uvula.

7. A dental orthosis for removable placement in the mouth and for engaging the upper and lower teeth of a user, comprising a main body element consisting essentially of:

an upper element having a curved shape which substantially corresponds to the shape of an upper dental arch, said upper element having an upwardly open tooth receiving trench for receiving at least a portion of at least some of the upper teeth;

a ramp element operatively coupled to and extending downwardly from said upper element and defining a ramp surface for engaging at least some of the lower anterior teeth, said upper element and said ramp element being interconnected and configured so that when the upper teeth of a user are received in the tooth receiving trench, the ramp element extends forwardly with respect to a vertical plane of the lower anterior teeth when the lower jaw of the user is in an unstressed position, so that engagement of the ramp surface and the lower anterior teeth positively shifts the lower jaw forwardly with respect to said unstressed position, and so that a predetermined gap between the upper and lower teeth is provided; and an aperture defined therethrough for allowing air to pass into and out of the mouth.

8. A device as in claim 7, wherein said main body is composed of a resilient semi-rigid polycarbonate resin thermoplastic body having a specific gravity of about 1.2, a tensile strength (yield) of about 9,000 PSI, and a softening temperature of about 310° F.

9. A device as in claim 8, wherein at least a portion of said body has a layer bonded thereto, said layer being composed of an ethylene-vinyl acetate copolymer resin having a softening and molding temperature of about 150° F.

10. A device as is claim 9, wherein said layer is bonded to at least all tooth-engaging surfaces of said body.

11. A device as in claim 10, wherein said layer is about 3 to 4 millimeters in thickness.

12. A device as in claim 9, wherein said layer is bonded to a interior surface of at least part of said trench and to said tooth engaging surface of said ramp element.

13. A dental orthosis for placement in the mouth to maintain a predetermined gap between and relative orientation of the upper and lower teeth to thereby reduce snoring by a user, comprising:

an upper element having a curved shape which substantially corresponds to the shape of an upper dental arch, said upper element having an upwardly open tooth receiving trench for receiving at least a portion of at least some of the upper teeth, said tooth receiving trench having a continuous forward wall and continuous rearward wall, each of which extend along substantially the entire extent of said upper element; and a ramp element operatively coupled to and extending downwardly from said upper element, said ramp element having a ramp surface for engaging at least some of the lower anterior teeth of the patient, said ramp element being operatively coupled to said upper element so that when the upper teeth of the patient are received in the tooth receiving trench of the upper element, the ramp element extends with respect to a vertical plane of the lower anterior teeth when the lower jaw is in an unstressed position so that engagement of said ramp surface and said lower teeth positively shifts the lower jaw forwardly with respect to said unstressed position.

14. A device as in claim 13, composed of a resilient semi-rigid polycarbonate resin thermoplastic body having a specific gravity of about 1.2, a tensile strength (yield) of about 9,000 PSI, and a softening temperature of about 310° F.

15. A device as in claim 14, further comprising a layer bonded to at least portion thereof, said layer being composed of an ethylene-vinyl acetate copolymer resin having a softening and molding temperature of about 150° F.

16. A device as is claim 15, wherein said layer is bonded to at least all tooth-engaging surfaces.

17. A device as in claim 16, wherein said layer is about 3 to 4 millimeters in thickness.

18. A device as in claim 15, wherein said layer is bonded to a interior surface of at least part of said trench and to said tooth engaging surface of said ramp element.

* * * * *